United States Patent [19]

Hach et al.

[11] 4,053,282
[45] Oct. 11, 1977

[54] METHOD AND APPARATUS FOR SAMPLING IMPURE WATER

[75] Inventors: Clifford C. Hach; Michael D. Buck, both of Ames, Iowa

[73] Assignee: Hach Chemical Company, Ames, Iowa

[21] Appl. No.: 661,604

[22] Filed: Feb. 26, 1976

[51] Int. Cl.[2] .................. G01N 1/10; G01N 21/00; G01N 33/18
[52] U.S. Cl. .................. 23/230 R; 23/253 R; 23/259; 73/425.6; 356/181
[58] Field of Search .................. 23/253 R, 259, 230 R; 356/36, 181; 73/425.6

[56] References Cited

U.S. PATENT DOCUMENTS

| | | | |
|---|---|---|---|
| 2,079,474 | 5/1937 | Walsh | 356/36 X |
| 2,797,149 | 6/1957 | Skeggs | 23/253 R X |
| 3,186,235 | 6/1965 | Ferrari | 23/253 R X |
| 3,334,018 | 8/1967 | Smythe | 23/253 R X |
| 3,401,591 | 9/1968 | Anthon | 356/36 |
| 3,524,366 | 8/1970 | Hrdina | 23/253 R X |
| 3,572,998 | 3/1971 | Anthon | 23/253 R |
| 3,692,490 | 9/1972 | Hall | 23/253 R |
| 3,826,615 | 7/1974 | Smythe et al. | 23/253 R X |
| 3,921,439 | 11/1975 | Burns | 23/253 R X |

Primary Examiner—Morris O. Wolk
Assistant Examiner—Arnold Turk
Attorney, Agent, or Firm—Leydig, Voit, Osann, Mayer & Holt, Ltd.

[57] ABSTRACT

A portion of a colorimetric liquid analyzer including a glass tube cell, a plunger mounted for reciprocation in the cell and having a passage to the cell, and a long liquid sample supply tube running from a body of liquid to be tested to the plunger passage. A "T" connector is provided in the tube and a pair of on-off valves which, together with the plunger, act to pump fixed volumes of fluid into and out of the cell. Means are provided to pump substantial air bubbles into the tube near its intake end, and the air bubbles are separated from the liquid through a vertical section of the T-connector so that only liquid is pumped into the cell. Preferably, acid is also added to the tube at its intake end to help dissolve particulate matter while the air bubbles continuously sweep the tube clean.

7 Claims, 1 Drawing Figure

U.S. Patent    Oct. 11, 1977    4,053,282
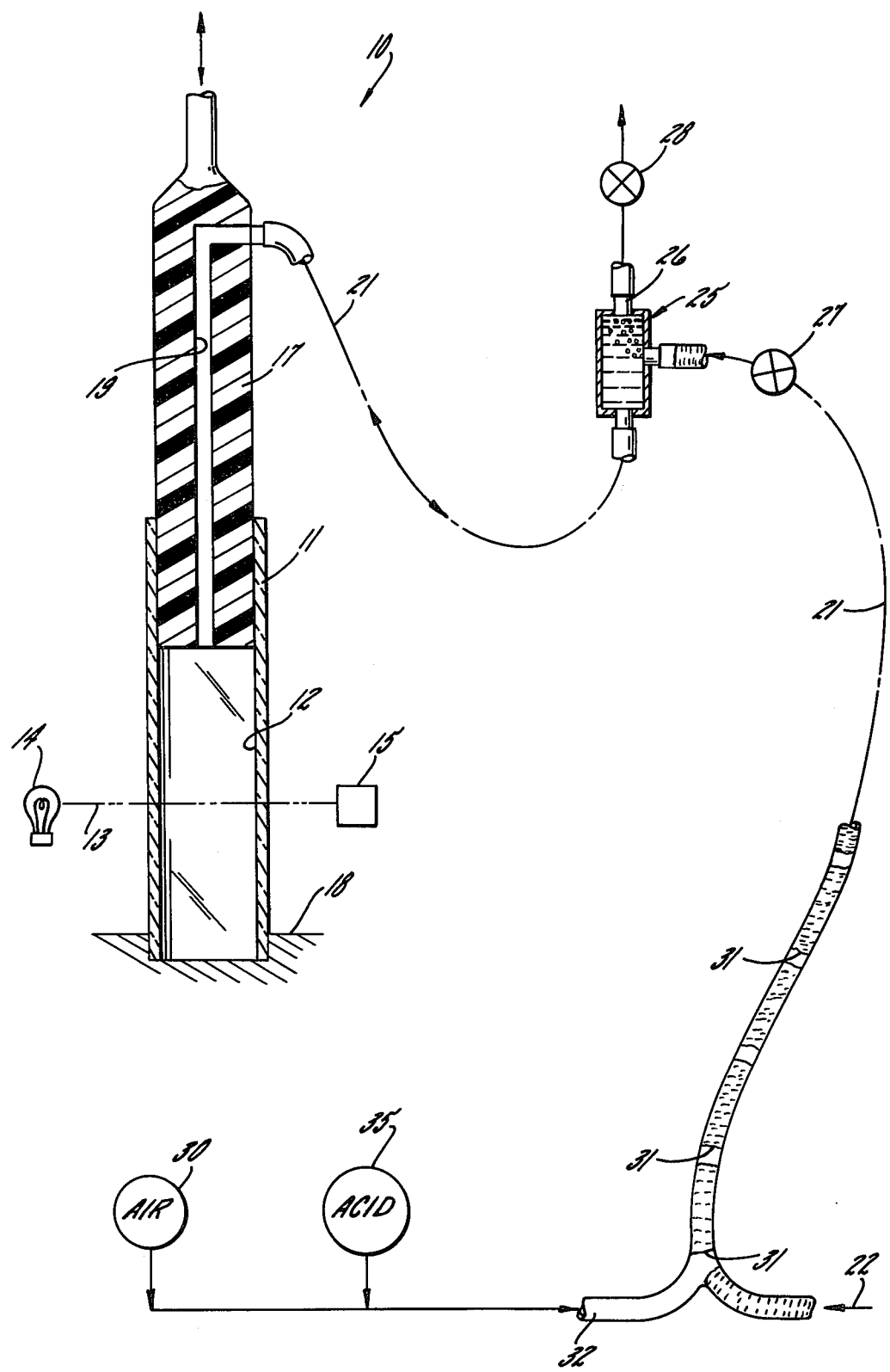

METHOD AND APPARATUS FOR SAMPLING IMPURE WATER

This invention relates generally to automatic analyzers and more particularly concerns a method and apparatus for drawing measured samples of impure water into an analyzer.

Analyzers for continuously monitoring water treatment systems have been well known. Typically, such instruments sample the water being monitored by taking discreet volumes, adding measured quantites of appropriate reagents for the tests being made, and reading the results colorimetrically with the information being displayed on a meter, fed to a continuous recorder or coupled to a high-low alarm device. The aim of such instruments is to reliably monitor for long periods of time on an automatic, no-operator attention, basis.

When sampling impure water such as sludge or sewage, it is difficult to keep the sample intake line unclogged and hence able to reliably deliver water to the analyzer. Even after filtering, impurities tend to coat and build up on the inner walls of sample intake tubing, thus creating a constant maintenance problem.

Another difficulty with colorimetric anaylzers is the effect of gas bubbles in the liquid sample upon the photoelectric system. Even a few minute gas bubbles will seriously distort the reading of a sensitive instrument. When cold impure water is being sampled, it is usually supersaturated and air bubbles tend to grow in the sample stream as it moves to and through the analyzer.

It is therefore an object of the invention to provide a method and apparatus for sampling impure water that keeps the sample intake line clear and open for long periods of operation. A collateral object is to provide such a method and apparatus that avoids adverse affects of air or other gas bubbles in the system.

Another object is to provide an apparatus as characterized above that is simple in design and thus economical to manufacture and maintain.

Other objects and advantages of the invention will become apparent upon reading the following detailed description, and upon reference to the drawing, in which:

The FIGURE is a schematic, fragmentary and partially sectioned analyzer embodying the invention.

While the invention will be described in connection with a preferred embodiment, it will be understood that we do not intend to limit the invention to that embodiment. On the contrary, we intend to cover all alternatives, modifications and equivalents as may be included within the spirit and scope of the invention as defined by the appended claims.

Turning to the drawing, there is shown a portion of a continuous, automatic colorimetric liquid analyzer 10 including a glass tube 11 defining a colorimetric cell 12 through which passes a light beam 13 from a lamp 14 to a photoelectric cell 15. A plunger 17 fits snugly in the tube 11 and is mounted for reciprocation from approximately the position illustrated, preferably establishing a cell 12 volume of 1.0 ml., to a position where the plunger 17 substantially fills the cell 12 and is in light contact with a supporting base 18.

The plunger 17 defines a passage 19 to the cell 12, and a liquid sample supply tube 21 extends from the passage 19 down into a body of liquid to be tested suggested by the arrow 22. Typically, in a plant treating sewage or sludge, the tube 21 could be 20 or 30 feet in length leading, from the settling tank for example, up to a suitable control and recording room. An analyzer of this kind is more completely dislosed in U.S. Pat. No. 3,953,136, issued Apr. 27, 1976, and assigned to the assignee of the present invention.

In carrying out the invention, a T-connector 25 is interposed in the tube 21 and defines a section 26 extending vertically from the tube 21, and a pair of on-off valves 27 and 28 are positioned to selectively close and thus block the section 26 and to selectively close and thus block the tube 21 between the connector 25 and the body of fluid being tested. The plunger 17 and the valves 27, 28 comprise a pump when they are properly sequenced by the analyzer 10. With the plunger 17 moved to completely fill the cell 12, the valve 28 is closed and the valve 27 is opened, whereupon movement of the plunger 17 to the position illustrated draws a fixed volume of fluid through the valve 27 into the cell 12. The valve 28 is then opened and the valve 27 closed, and thus return movement of the plunger 17 expels the liquid from the cell 12 and wipes the walls of the cell tube 11 clean, readying the analyzer to draw in another sample. The expelled liquid moves through the then opened valve 28 and, as shown in the application referred to above, the valve 28 may direct the water sample to reagent adding pumps and a second colorimetric cell.

In accordance with the invention, a pump 30 periodically injects substantial air bubbles 31 into the tube 21 through a branch line 32 adjacent the supply tube end that is in the body of liquid to be tested. In the case mentioned where the plunger 17 draws 1.0 ml. of water into the cell 12 per stroke, air bubbles of about 0.2 ml. per stroke in a tube 21 whose internal diameter is approximately 1/16 to ⅛ inch are sufficiently substantial to perform as intended. It has been found that such air bubbles 31 continuously sweep the tube 21 clean, thereby preventing any build-up of solid material even when the water portion of sewage or sludge is being tested. Preferably, a second pump 35 is utilized to add, through the line 32, small amounts of acid to the liquid samples moving along the tube 21. The acid helps dissolve particulate matter which might be carried in the water to be tested.

As previously mentioned, it is highly undesirable to allow a bubble to enter, or to form in, the cell 12 since such bubbles erratically affect light transmittance. In the analyzer 10, the air bubbles injected into the line 21, together with whatever additional bubbles are formed as a result of drawing in and warming cold supersaturated water, move up to and collect at the top section 26 of the T-connector 25. The plunger 17 draws only liquid, without air bubbles, from the lower portion of the connector and, on the plunger stroke expelling liquid from the cell 12, the expelled liquid flushes the air bubbles from the connector through the section 26 and the valve 28.

What therefore appear to be the incongruities of adding air bubbles to a system where air bubbles are to be avoided, and of desiring to draw in a fixed volume of liquid from a line in which large air bubbles are added, are resolved by the action at the T-connector 25. The cleaning action of the air bubbles 31 in the tube 21 is retained, while the air and liquid are separated in the connector 25 close to the cell 12. Preferably, a screen or filter is also provided at the intake end of the tube 21.

Those familiar with this art will appreciate that the system described is quite simple in design and thus economial to manufacture and maintain.

We claim as our invention:

1. In a liquid analyzer having a colorimetric cell and a pump for pulling liquid into said cell and expelling liquid from the cell, the combination comprising, a liquid sample supply tube running from a body of liquid to be tested to said pump, means for injecting substantial air bubbles into said tube adjacent the tube end in said body of liquid, and a T-conector in said tube near the tube end at said pump, said connector having a vertically extending section for collecting gas bubbles and a lower section connected to said pump for supplying liquid without bubbles to said pump and receiving liquid from said pump for ejection of said gas bubbles from said T-connector.

2. The combination of claim 1 including means for injecting small charges of acid into said tube along with said air bubbles to help dissolve particulate matter in said liquid.

3. The combination of claim 1 in which said tube is approximately 1/16 to ⅛ inches in internal diameter and said air bubbles are approximately 0.2 ml. in volume.

4. In a liquid analyzer, the combination comprising, a glass tube defining a colorimetric cell, a plunger mounted for reciprocation in said tube and containing a passage to said cell, a liquid sample supply tube running from a body of liquid to be tested to said plunger passage, a T-connector in said tube having a section extending vertically from the tube, a pair of on-off valves for respectively closing said tube between the connector and the body of liquid and said vertically extending section, said plunger and said valves thus comprising a pump for pulling a fixed volume of liquid into the cell through said T-connector section from said body of liquid and expelling the liquid from the cell through said T-connector section, and means for injecting substantial air bubbles into said tube adjacent the tube end in said body of liquid so that the spaced bubbles along the tube continuously sweep the tube clean.

5. The combination of claim 4 including means for injecting small charges of acid into said tube along with said air bubbles to help dissolve particulate matter in said liquid.

6. The method of sweeping clean the liquid sample supply tube of an automatic analyzer comprising, in combination, the steps of injecting substantial air bubbles at the intake end of said tube, separating by gravity the air bubbles from the liquid at a point near the analyzer, drawing liquid samples for analysis from the liquid after air-liquid separation, and expelling the liquid sample after analysis through the air-liquid separation region so as to flush out accumulating air bubbles.

7. The method of claim 6 including the step of adding small charges of acid at the intake end of said tube to help dissolve particulate matter in said liquid.

* * * * *